United States Patent [19]

Dragan

[11] 4,084,319
[45] Apr. 18, 1978

[54] FACE BOW

[76] Inventor: William Basil Dragan, R.F.D. No. 1 Burr St., Fairfield, Conn. 06430

[21] Appl. No.: 710,551

[22] Filed: Aug. 2, 1976

[51] Int. Cl.$^2$ .............................................. A61C 9/00
[52] U.S. Cl. ..................................................... 32/21
[58] Field of Search .................... 32/14 B, 19, 20, 21, 32/32

[56] References Cited

U.S. PATENT DOCUMENTS

| 2,334,643 | 11/1943 | Moore | 32/32 |
| 2,403,366 | 7/1946 | Horuat | 32/21 |

*Primary Examiner*—Robert Peshock

*Attorney, Agent, or Firm*—Arthur T. Fattibene

[57] ABSTRACT

A face bow for fabricating occlusal restorations which can be readily adapted to several different types of known articulators and which face bow has toggle and bite fork assembly which is rendered readily removeable after the impressions of one of the jaw teeth has been made, whereby casts of such impressions can be made without tying up the entire face bow assembly.

An embodiment of the face bow is further constructed so as to compensate for any bi-lateral asymmetrical difference of a patient's left and right condylar distances.

11 Claims, 10 Drawing Figures

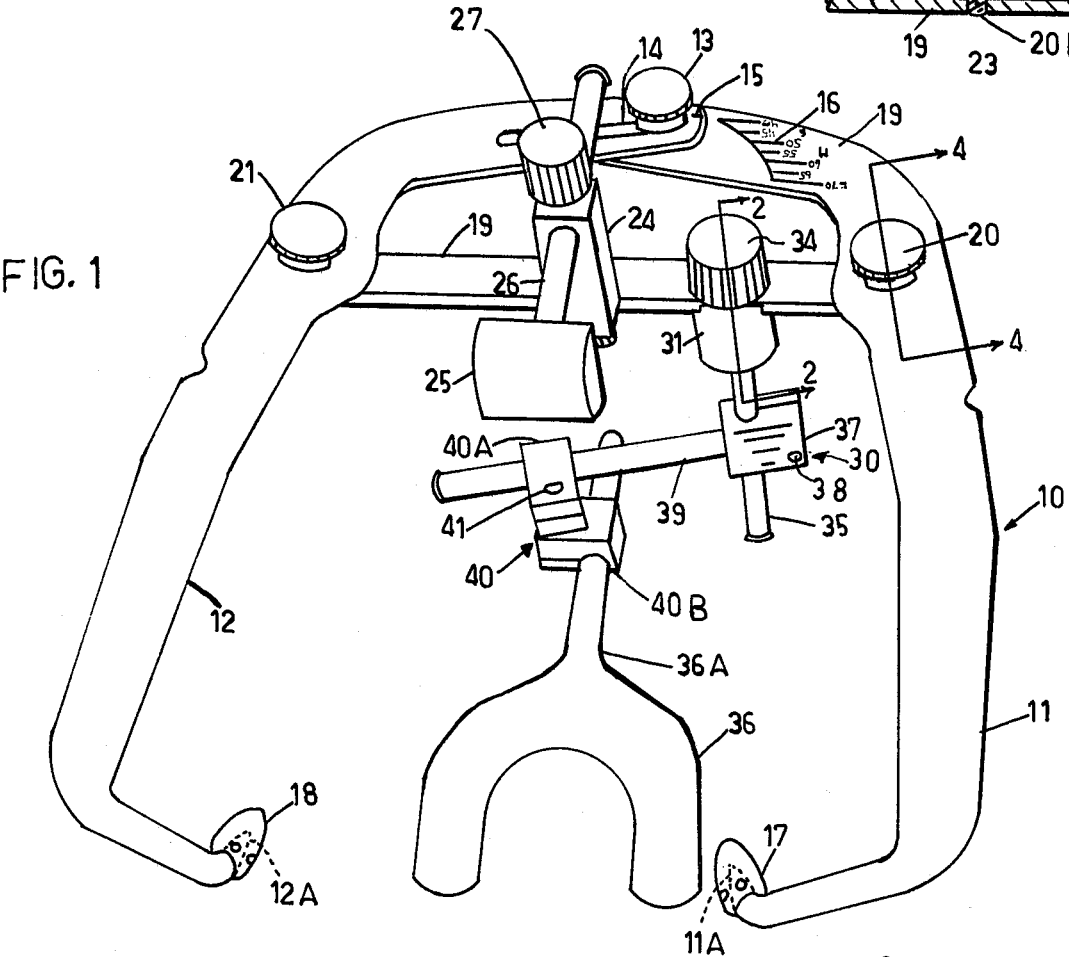
FIG. 1
FIG. 4
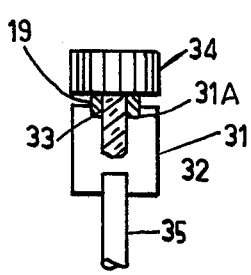
FIG. 3
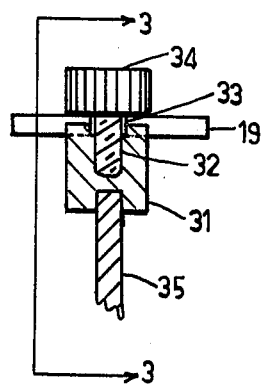
FIG. 2

U.S. Patent April 18, 1978 Sheet 3 of 3 4,084,319
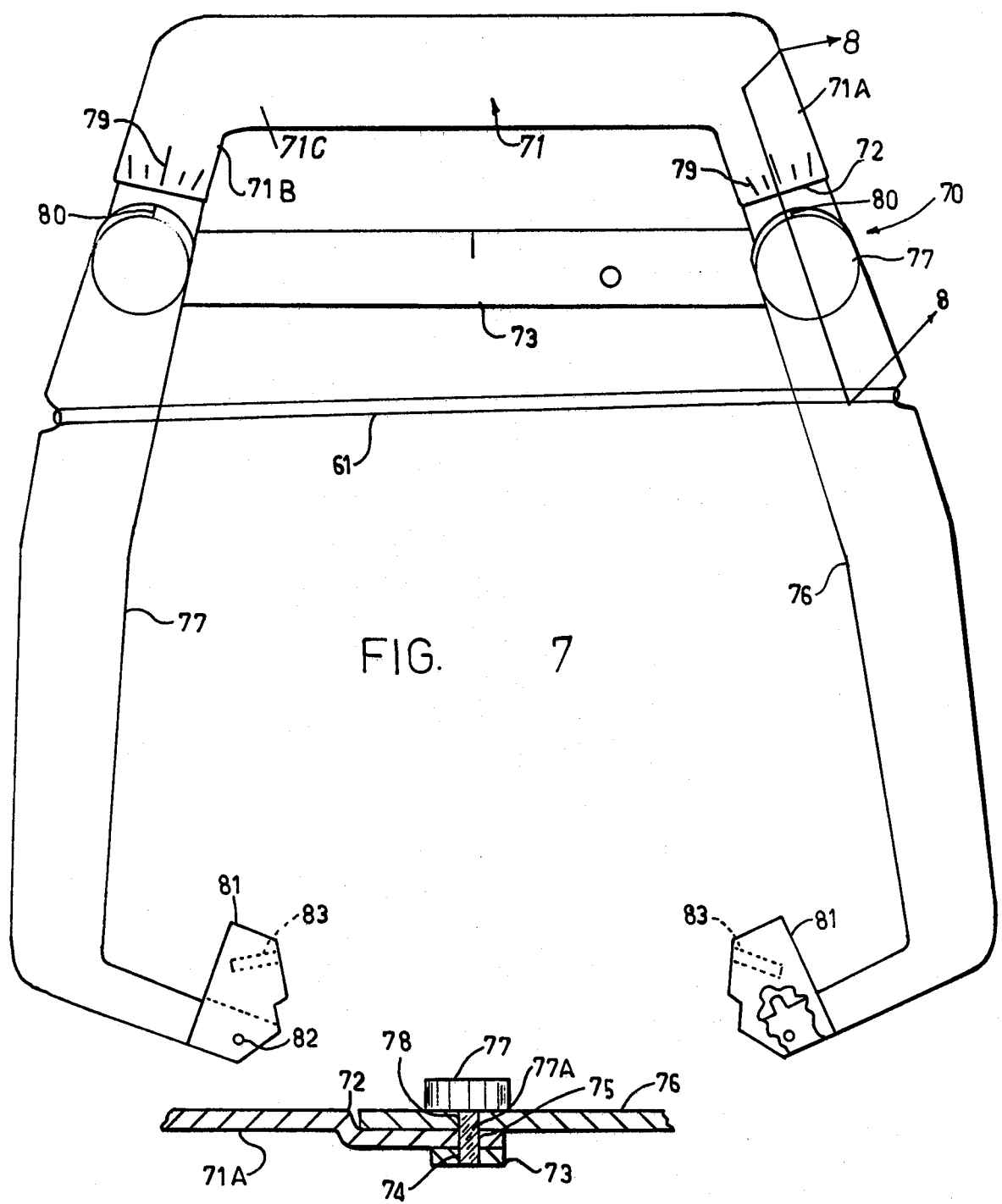
FIG. 7
FIG. 8
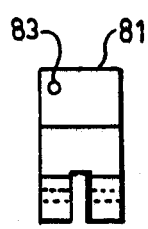
FIG. 10
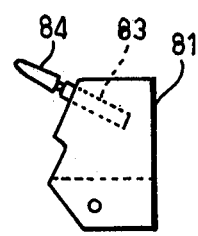
FIG. 9

FACE BOW

PROBLEM & PRIOR ART

To effect occlusal restorations, it is necessary for a dentist or dental technician to simulate the mandible and maxilla relationship of a patient's jaw for reproducting the relative movements thereof. Heretofore this has been attained by a dentist utilizing a face bow to take an impression of one's bite relative to the orbital plane of the patient's head. The face bow with the bite impression is then transferred to an articulator so that the casts of a patient's mandible and maxilla can be set relative to the impressions of one's bite so that the relationship of casts can be maintained in a manner simulating the patient's jaw movements.

There are presently on the market, a number of various types of articulators, i.e., Whip Mix, Ney, Dentatus, Denar, Hanan, Simulator, Stuart and the like. Each such articulator requires a complementary face bow. The constructions of the known face bows are such that they were not readily interchangeable, and thus a given face bow was usable with only a specific articulator.

Also, it was heretofore customary that after a dentist made a bite impression utilizing a specific face bow whereby the bite fork was fixed relative to the orbital plane, the entire assembly of the face bow with its associate bite fork was tied up until the casts were made and set to the given articulator. Accordingly, it was impressive that a dentist working with occlusal restorations was required to have numerous face bow assemblies on hand. As such face bow assemblies constitute a relative large capital expenditure, a dentist was obliged to make a substantial investment in face bows.

It is also noted that the known face bows constructions were made so that the setting of the face bows did not take into consideration that a patient's left and right condylar distances are generally not symmetrical. This was because the known face bows were constructed so that their respective arms were so connected that any setting of the face bow to a patient caused the arms to be laterally displaced an equal amount. As a result, the setting of the known face bows to a patient did not provide for any adjustment to compensate for any asymmetrical difference between a patient's left and right condylar distances. Because of the inability of the known face bows to compensate for any bi-lateral asymmetrical differences between the left and right condylar distances of a particular patient, a true and accurate reproduction of one's bite relative to the orbital plane of a patient's head was not truely attainable.

OBJECTS

It is therefore an object of this invention to provide a face bow which can be readily adapted for use with several different types of known articulators.

Another object is to provide a face bow construction in which the bite fork can be readily removed from its face bow assembly whereby only the bite fork and associated toggle need be tied up during the making and/or placing of the cast of one's bite onto an articulator for simulating one's jaw movements.

Another object is to provide a face bow construction in which any bi-lateral asymmetry of a patient's left or right condylar distance can be readily compensated so as to provide for a more accurate reproduction of one's bite relative to one's orbital plane.

BRIEF SUMMARY OF INVENTION

The foregoing objects and other features of this invention are attained by a face bow comprising a pair of arms which has one end thereof inturned for insertion into the depression anterior and medial to the tragi of a patient's ear. The inturned ends of the side arms have an ear piece connected thereto. The respective ear pieces are formed so as to complement the condylar elements of a given articulator. The ear pieces are rendered readily removeable so that by changing the ear piece the face bow is readily adapted for use with a given corresponding articulator.

The other end of the side arms are pivotally connected for effecting adjustment thereof. Interconnected between the side arms is a cross bar to which a toggle and bite fork is connected. In accordance with this invention, the toggle and bite fork assembly is rendered readily removeable so that the toggle and bite fork can be removed and put aside until the casts are mounted or sent to the laboratory. In this manner, the face bow is not tied up with one particular case.

An embodiment of this invention contemplates that the respective arms of the face bow are independently adjusted to a fixed base so that any bi-lateral asymmetry of a patient's left or right condylar distances can be readily compensated. In this manner a more accurate reproduction of one'bite relative to the orbital plane can be achieved.

FEATURES

A feature of this invention resides in providing a face bow with readily interchangeable ear pieces so that the face bow can be readily adapted for use with various types of articulators whereby the respective interchangeable ear pieces complement the condylar pivots of a given articulator.

Another feature resides in the provision of rendering the toggle and bite fork assembly readily disconnectable so that the same can be removed from the face bow after the impressions have been made.

Another feature resides in the provision of indices whereby the intercondylar distances can be read on a plurality of different scales, e.g., in millimeters and/or small, medium or large.

Another feature resides in the provision of a face bow having independently adjustable side arms so that any asymmetry of a patient's intercondylar distances can be readily compensated.

Other features and advantages will become more readily apparent when considered in view of the drawings and specification in which:

FIG. 1 is a perspective view of a face bow embodying the present invention.

FIG. 2 is a detailed sectional view taken on line 2—2 on FIG. 1.

FIG. 3 is a detailed sectional view taken on line 3—3 on FIG. 2.

FIG. 4 is a detailed sectional view taken on line 4—4 on FIG. 1.

FIG. 7 is a plan view of another modified embodiment.

FIG. 8 is a detail sectional view taken along line 8—8 on FIG. 7.

FIG. 9 is a detail plan view of a detachable ear piece.

FIG. 10 is a left end view of the ear piece of FIG. 9.

Figure 5:
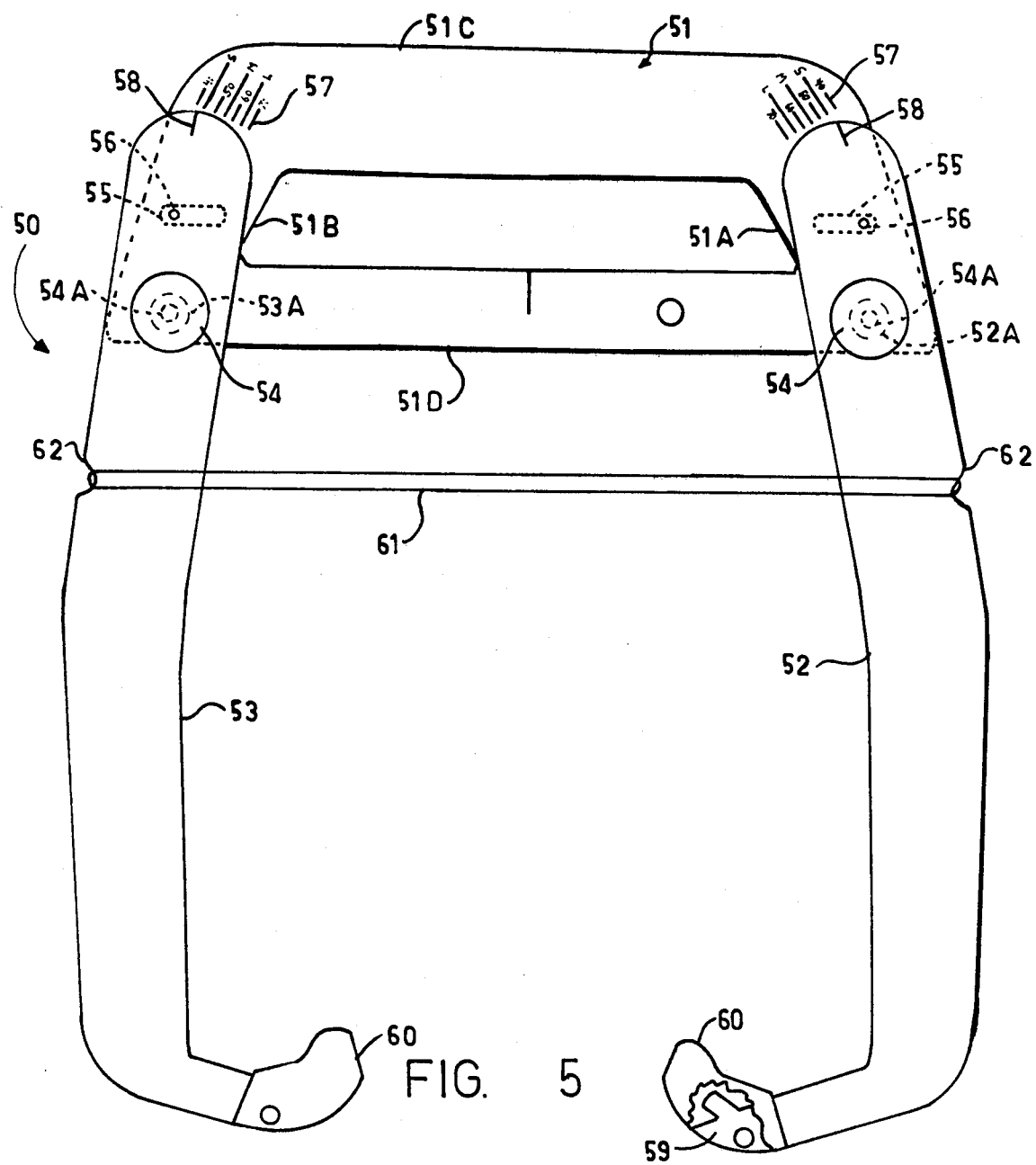
FIG. 5 is a plan view of a modified face bow construction with the nasion gauge and bite fork toggle assembly removed.

Referring to the drawings there is shown in FIGS. 1 to 3 a face bow 10 embodying the present invention. The face bow 10 comprises a pair of side arms 11 and 12 which are pivotally connected about a pivot 13. In the illustrated embodiment, the pivot 13 comprises a lock screw which has a thread stem portion which extends through a slotted opening 14 on one side arm 12 and which threads into a threaded hole formed in the other arm 11. It will be apparent that when the lock screw or pivot 13 is loosened, that the respective side arms can be adjusted to a given patient.

As seen in FIG. 1, a scribe mark or index 15 is located on the end of side arm 12. A complementary scale 16, e.g., a millimeter scale ranging between 45 to 70 is disposed in the other arm 11. The arrangement is such that the intercondylar distance between the ear pieces 17 and 18 can be readily determined in millimeters. Also the arms 11 and 12 may be provided with an alternate scale 19 whereby the intercondylar distance can be read in the well known small, medium and large sizes.

In accordance with this invention, the ear piece 17 and 18 are formed of a suitable plastic material and they are detachably secured to the inturned ends 11A and 12A of the respective arms 11 and 12. In the illustrative embodiment, the ear pieces 17 and 18 are specifically formed so that they are rendered compatible with a given articulator. Since each given articulator has a condylar mount of specific construction the ear piece is designed to complement the condylar mounts of a given articulator. In the form illustrated in FIG. 1, the ear piece is provided with a hole for receiving a complementary pin of an articulator's condylar mounts. Also by rendering the respective ear pieces readily removeable, they can be readily interchanged so that the face bow can be adapted to any of a given number of different articulators by the attachment of an appropriate complementary ear piece. Also, the ear pieces being removeable can be readily sterilized, if necessary, and/or rendered disposable.

Interconnected between the side arms 11 and 12 is a cross bar 19. The cross bar is fixedly secured in the adjusted position by lock screws 20 and 21, which when lossened permits the side arms 11 and 12 to pivot to an adjusted position. As best seen in FIG. 4, the lock screw 20 has a head portion 20A and a connected threaded stem 20B which extends through a hole 22 in side arm 11 and engages a tapped hole 23 in arm 19. Lock screws 21 is similarly constructed. It will thus be apparent that the respective side arms 11 and 12 can be readily locked in adjusted position by tightening lock screws 13, 20 and 21.

Mounted on the cross bar intermediate the ends thereof is a bracket 24 which is suitably connected thereto. Adjustably mounted in bracket 24 is a nasion gauge 25. The nasion gauge 25 is mounted on the end of a shaft 20 which is slideably mounted on bracket 24. A set screw 27 secures the nasion shaft in the adjusted position.

According to this invention a toggle and bite fork assembly 30 is detachably connected to the cross bar 19. The assembly 30 includes boss 31 which has a notch 31A for receiving the cross bar 19. The boss is provided with a tapped hole 32 disposed in alignment with a hole 33 formed in the cross bar 19. A lock screw 34 secures the toggle assembly to the cross bar; so that it can be readily detached from the cross bar 19 by unscrewing the lock screw 34.

Depending from boss 31 is a stem 35 for adjustably supporting the bite fork 36 for vertical adjustment. A sliding bracket 37 is adjustably mounted on stem 35. The bracket 37 comprises a split member which is slideably mounted on stem 35, and which is frictionally locked in place by a set screw 38 or the like. Projecting laterally of the bracket is a rod 39 on which a universal joint 40 is mounted. The universal joint 40 includes a first member 40A which is slideable along the rod 39. Pivotally connected to the first member 40A is a second member 40B. The pivot 41 about which members 40A and 40B are pivoted is such that when tightened the respective members 40A and 40B can be locked in the adjusted position.

Adjustably mounted on member 40B is the stem portion 36A of the bite fork 36. When the pivot 41 is tightened it will also cause the stem portion 36A to be frictionally secured to the universal member 40A. Both members 40A and 40B comprise a split type clamp which are secured respectively to rod 39 and stem 36A.

In operation, the bite fork with suitable wax thereon is placed into the patient's mouth whereupon the patient closes onto the fork into centric relation to form the bite impression. The face bow 10 described is then fitted to the patient's face while maintaining the bite. With the appropriate ear pieces 17, 18 connected to the end of side arms 11 and 12, the patient guides the ear pieces into his ears. The toggle assembly is then placed on the cross bar 19 with the stem 36A of the bite fork 36 fitted to member 40A, and with the respective toggle members lossely mounted relative to the stem 36A and each other. The nasion gauge 25 is then adjusted to the patient and tightened in adjusted position by lock screw 27. With the adjustment made, the three lock screws 13, 20 and 21 of the face bow are tightened to fix the intercondylar distance of the patient. The toggle and bite fork assembly is then tightened to secure the adjusted position.

At this point, with all adjustments secured, the dentist can now read on the scale 16 or 19 provided, the intercondylar distance in millimeters and/or to a given standard size, e.g., small, medium or large.

With the intercondylar distance noted and recorded, and the bite impression formed, the dentist can effect the removal of the face bow 10. This is attained by first lossening the nasion gauge 25, by the lossening lock screw 27, and thereafter lossening the face bow lock screws 13, 20 and 21. This permits the face bow 10 to be removed.

In accordance with this invention, the toggle assembly which has been fixedly secured in adjusted position to stem 35 thereof can be readily removed from the cross bar 19 without disturbing the setting thereof by simply loosening lock screw 34. Thus the toggle assembly 30 fixed to a set position can be marked with the patient's name and intercondylar reading, and put aside until the casts are mounted or sent to the laboratory. In the meanwhile, the dentist would have the face bow available for use on another person.

To make the cast or to mount the cast of the patient's bite to an articulator of any specific type, the laboratory or dentist merely sets the articulator to the intercondylar reading or size of the patient whose bite impression was taken. The toggle assembly 30 is then attached to the cross bar of the face bow. Since the toggle assembly containing the bite impression has not been disturbed, the dentist or laboratory technician can readily reestablish a relationship of the patient's bite relative to the patient's orbital plane.

By attaching the appropriate ear pieces to the end of the face bow side arms, the face bow with the toggle and bite fork 30 fixed thereto can be mounted to a given articulator and the casts secured to the upper and lower members of the given articulator in the well known manner. Thus the relationship of the bite impression of a given patient relative to the orbital plane of a patient can be re-established or transferred to any of several different articulators by the proper selection of ear pieces which complement the condylar mounts of a given articulator. In those articulators which require the orbital plane to be maintained parallel to the upper member of the articulator, a suitable shim may be provided to position the face bow relative to the articulator.

Figure 6:
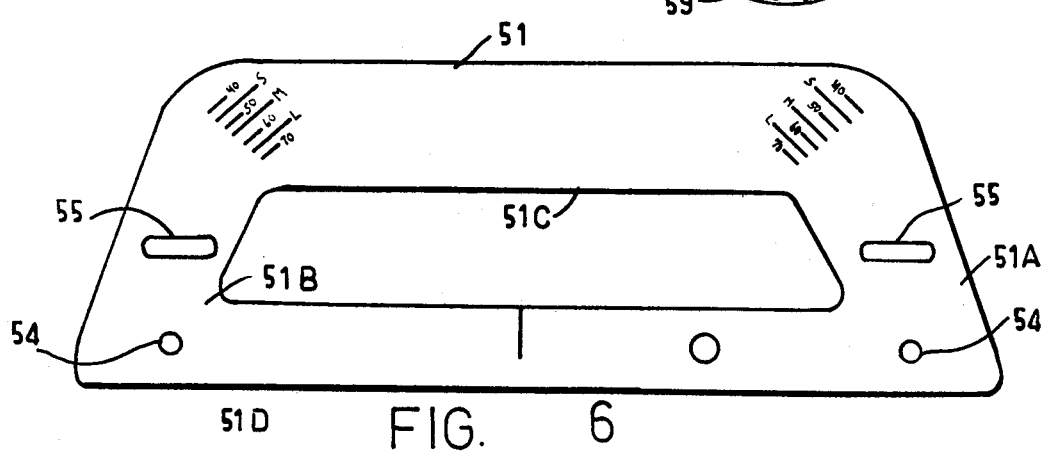
FIG. 6 is a detail plan view of the base member of the face bow of FIG. 5.

FIGS. 5 and 6 illustrate a modified form of the invention. The face bow 50 of FIG. 5 comprises a fixed base member 51, which includes a pair of opposed spaced apart leg portions 51A and 51B interconnected by a web portion 51C. A cross bar 51D is integrally connected between the extended ends of the leg portions 51A and 51B. Thus as best seen in FIG. 6, the fixed based member comprises a generally D shaped member.

Connected to the extended end of the respective leg portions 51A and 51B are side arms 52 and 53. The respective side arms 52 and 53 are pivotally connected to the leg portions 51A and 51B for movement relative thereto. The pivot means comprises a headed stud or screw 54 which has a threaded shank 54A, which extends through an aperture 52A and 53A formed in arms 52 and 53 and which is threaded into a tapped hole 54 of the base member 51.

Thus when the pivot screw 54 is loosened, the respective arms 51 and 52 can be readily adjusted about the pivot. To secure the arms 52 and 53 in the adjusted position, the pivot screw 54 need only be hand tightened.

As shown in FIGS. 5 and 6, the base member is provided with a slot 55 disposed intermediate the leg portions 51A, 51B for accommodating a pin 56 connected to each arm 52, 53. The pin 56 and slot 55 thus cooperate to define the limits between which arms 52 and 53 can be pivoted relative to the base member 51.

As shown, the base member 51 is provided with indicia 57 which complements with a marking 58 whereby a reading may be had of a patient's left or right condylar distance relative to the center line of the face, mid saggital plane. It will be understood that the reading or markings 57 may be to any suitable scale, e.g., inches, or millimeters.

The ends of the respective arms 52 and 53 are inturned as at 59 and are formed for accommodating a detachable ear piece 60 as hereinbefore described with respect to FIG. 1.

To complete the assembly, it is understood that nasion gauge 24 and a bite fork toggle assembly 30, similar to that described with respect to FIGS. 1 to 4 are fitted to the cross bar 51D. However, the nasion gauge 24 and toggle assembly 30 have been omitted in FIGS. 5 and 6.

With the face bow construction 50 of FIGS. 5 and 6, the arrangement is such that the respective side arms 52 and 53 can be independently set and thereby any bi-lateral asymmetry of a patient's left or right intercondylar distances can be set. With such described construction, any inaccuracies previously encountered as a result of the asymmetry of the left and right condylar distances can be readily compensated.

To maintain the side arms 52 and 53 under a spring like bias, a rubber band 61 can be stretched between the side arms 52 and 53, as shown in FIG. 5. Suitable notches 62 may be formed in the side arms 52 and 53 for positioning the elastic band 61.

The cooperating pin 56 and slot 55 thus cooperates to limit the movement of the arms relative to the base, and also prohibits the arms from closing onto a dentist hand during the handling of the face bow 50.

In all other respects the operation and use of face bow 50 is similar to that hereinbefore described with respect to the face bow of FIGS. 1 to 4.

FIGS. 7 to 10 illustrate another modified face bow construction 70. In this form of the invention, the face bow 70 comprises a generally C shaped base member 71, having opposed leg portions 71A, 71B interconnected by a web or bight portion 71C. As best seen in FIG. 8, the respective leg portions 71A & 71B are offset intermediate the ends thereof as indicated at 72.

Connected between the free ends of the leg portions 71A and 71B is a cross bar 73. The cross bar 73 is provided in a tapped hole 74 adjacent the ends thereof which are disposed in alignment with a hole 75 formed on the end of the respective leg portions 71A and 71B.

As described with respect to FIGS. 5 and 6, side arms 76 and 77 are pivotally connected to the offset leg portions 71A and 71B. The pivotal connecting means comprises a headed screw 77 having a threaded shank 77A which extends through aligned holes 78 and 75 formed in side arms 76, 77 and the leg portions of the fixed member 71 respectively. The end of the screw shank is threaded into the tapped hole 74 of the cross bar.

With the construction described, the respective arms 76 and 77 are independently adjusted and fixed to the base member as hereinbefore described with respect to FIGS. 5 and 6. Thus the left and right condylar distances can be independently set to accommodate for any asymmetry of a patient's intercondylar distance.

The raised portion of the respective leg portions 71A and 71B are provided with markings or indicia 79 which cooperates with a marking or index 80 formed on the end of the corresponding side arms whereby the left and right condylar distances can be read.

The other ends of the respective side arms are adapted with a detachable ear piece 81. As shown one end the respective ear pieces 81 is bifurcated whereby it can be received on the inturned end of the respective side arms, a pin 82 extending through the bifurcated end portion detachably secures the ear piece 81 to the side arm 76 or 77.

The respective ear pieces 81 are provided with a hole or bore 83 which is adapted to receive the pivots of the condylar mounts of a particular articulator or conversely the ear piece 81 may be fitted with a mounting pivot pin 84, as shown in FIG. 9, which can then be supported to the condylar mount of an articulator. Thus, the ear piece is provided with a versitility whereby the face bow can be readily adapted to any of several known articulators.

In this form of the invention, it will be understood that the nasion gauge and fork bite toggle assembly can be detachably secured to the cross bar 71 as hereinbefore described. Thus in operation, the face bow 70 is similar to that of face bow 50.

The operation of face bows 40 and 70 are similar in that a dentist can independently set the left and right condylar distance of a patient. Therefore to make a cast of one's bite with the face bow construction of FIGS. 5 and 6 or 7 and 10, the dentist records the left and right condylar distance of the patient so that the same intercondylar distance can be re-established in the laboratory.

With any of the described structures, it will be apparent that the casts of one's bite can be readily made by merely transmitting the fixed toggle assembly to a laboratory together with the condylar readings.

From the foregoing descriptions, it will be noted that the specific face bows described enables a dentist to freely use the face bow arms while the casts are being set or sent to the laboratory and thereby greatly reducing the need of having on hand numerous face bow arms. Also by rendering the ear pieces interchangeable, the face bow can be readily adapted for use with any of several differently available articulators.

While the present invention has been described with respect to a particular embodiment, it will be appreciated and understood that variations and modifications may be made without departing from the spirit and scope of the invention.

What is claimed is:

1. A face bow comprising:
   a pair of side arms having one end thereof inturned for insertion into the depression anterior and medial to the tragi of a patient's ears,
   an ear piece detachably connected to the inturned end of each of said side arms, said ear piece being adapted to be inserted in a patient's ear when said face bow is fitted to a patient and adapted for mounting said face bow to a given articulator.
   a cross bar interconnected between said side arms intermediate the length thereof about which said side arms pivot for adjusting said side arms to a patient's intercondylar size,
   means for connecting the other ends of said side arms for facilitating said adjustment for said intercondylar size and for securing said side arms in said adjusted position,
   indicies means formed on said side arms for indicating said intercondylar size,
   a nasion gauge means mounted on said cross bar for engaging the nasion when fitted to a patient,
   a bite fork for supporting an impression of a patient's bite,
   a toggle means for adjustably supporting said bite fork to said cross bar,
   and means for detachably connecting said toggle means and bite fork supported thereon to said cross bar whereby said toggle means and bite fork secured thereby can be readily removed and put aside until the casts are to be mounted thereon whereby the mandible and maxilla relationship of one's bite relative to the oribital plane of the patient's head is maintained and which relationship can be readily re-established to a given articulator.

2. The invention as defined in claim 1 wherein said ear pieces include means for adapting said face bow to a given articulator.

3. The invention as defined in claim 1 wherein said toggle means includes a bracket,
   a vertical rod depending from said bracket,
   a slider adjustably mounted on said rod,
   a lateral rod extending from said slider,
   and a universal clamp slideably mounted on said lateral rod,
   said bite fork having a stem whereby said bite fork is secured to said universal clamp.

4. The invention as defined in claim 3 wherein said universal clamp comprises a first clamp means and a second clamp means pivotally connected,
   said first clamp means being adjustably positioned along said lateral rod,
   and said second clamp means being adjustably positioned relative to said bite fork stem.

5. A face bow for fabricating occusal restorations and which is universally adapted to a plurality of differently constructed articulators comprising:
   a pair of side arms having one end thereof inturned for insertion in the depression anterior and medial to the tragi of a patient's ear,
   a plurality of interchangeable pairs of ear pieces,
   each said pair of ear pieces being adapted to complement the condylar elements of a specific articulator,
   said ear pieces being detachably connected to the inturned ends of said side arms whereby said face bow can be readily adapted for use to a particular articulator by interchanging said pairs of each pieces,
   a cross bar interconnected between said side arms intermediate the ends thereof about which said side arms can pivot for adjusting said side arms to a patient's intercondylar size,
   means for securing the other ends of said side arms in the intercondylar adjusted position,
   indicia means for indicating said adjusted intercondylar size,
   a nasion gauge means mounted on said cross bar adapted to engage the nasion when said face bow is fitted to a patient,
   a bite fork for supporting an impression of a patient's bite,
   toggle means for supporting said bite fork to said cross bar in an adjusted position,
   and means for detachably connecting said toggle means on said cross bar whereby said toggle means and connected bite means can be readily removed and sent to a lab for the casts to be mounted whereby the mandible and maxilla relationship of one's bite relative to the orbital plane of a patient's head is maintained.

6. A face bow comprising:
   a fixed base member having opposed spaced apart leg portions,
   a side arm having one end thereof connected to each of said leg portions,
   means for individually pivotally connecting said side arms to said respective leg portions and for securing said side arm in its respective adjusted position,
   each of said side arms having the other end thereof inturned for insertion into the depression anterior and medial to the tragi of a patient's ear,
   an ear piece detachably connected to the inturned end of said side arms,
   a cross bar interconnected between the opposed leg portions of said base member,
   a nasion gauge means detachably connected to said cross bar,
   a bite fork for supporting the impression of a patient's bite, a toggle means for supporting said bite fork relative to said cross bar, and means for detachably connecting said toggle means and connected bite fork on said cross bar whereby said toggle means and bite fork secured thereto can be readily removed from said cross bar whereby the mandible and maxilla relationship of one's bite relative to the orbital plane of the head is maintained.

7. The invention as defined in claim 6 and including indicia means formed on the respective leg portion of said base member, and each side arm having a complementary indicia to indicate the respective left and right condylar distance relative to the centerline of said face bow.

8. The invention as defined in claim 7 wherein said base member and said cross bar are integrally formed.

9. The invention as defined in claim 8 wherein each of said leg portions has a slot formed therein, a pin connected to each of said side arms, said pin being received within said slot whereby said slot and pin cooperate to determine the limits of adjustments of said side arms.

10. The invention as defined in claim 6 and including an elastic band stretched between said side arms for maintaining a bias on said side arms.

11. A face bow comprising:

a base member having opposed spaced apart leg portions, a side arm having one end thereof connected to each of said leg portions, means for individually pivoting and adjusting the setting of the respective side arms relative to the connected leg portions of said base, a cross bar connected between said leg portions, a nasion gauge connected to said cross bar, said nasion gauge being adapted to engage a patient's nasion when said face bow is fitted to a patient's head, and a toggle and bite fork assembly connected to said cross bar, and including means for detachably connecting said toggle and bite fork assembly to said cross bar whereby the mandible and maxilla relationship of one's bite relative to the orbital plane of a patient's head is maintained.

* * * * *